US011433231B2

(12) United States Patent
Leonhardt (10) Patent No.: US 11,433,231 B2
(45) Date of Patent: Sep. 6, 2022

(54) BIOELECTRIC STIMULATION FOR SONIC HEDGEHOG EXPRESSION

(71) Applicant: LEONHARDT VENTURES LLC, Corona Del Mar, CA (US)

(72) Inventor: Howard J. Leonhardt, Corona Del Mar, CA (US)

(73) Assignee: LEONHARDT VENTURES LLC, Mission Viejo, CA (US)

( * ) Notice: Subject to any disclaimer, the term of this patent is extended or adjusted under 35 U.S.C. 154(b) by 0 days.

(21) Appl. No.: 16/847,351

(22) Filed: Apr. 13, 2020

(65) Prior Publication Data

US 2020/0324106 A1 Oct. 15, 2020

Related U.S. Application Data

(60) Provisional application No. 62/834,309, filed on Apr. 15, 2019, provisional application No. 62/988,345, filed on Mar. 11, 2020.

(51) Int. Cl.
*A61N 1/36* (2006.01)
*A61N 1/04* (2006.01)

(52) U.S. Cl.
CPC ....... *A61N 1/0472* (2013.01); *A61N 1/36034* (2017.08)

(58) Field of Classification Search
CPC ............. A61N 1/0472; A61N 1/0492; A61N 1/36034; A61N 1/0428; A61N 1/0452;
(Continued)

(56) References Cited

U.S. PATENT DOCUMENTS 9,855,418 B2 1/2018 Haralambidis
10,342,968 B2 7/2019 Hasui et al.
(Continued)

FOREIGN PATENT DOCUMENTS

WO 2014/172693 A2 10/2014

OTHER PUBLICATIONS

Carol A. Podlasek, David J. Zelner, Hong Bin Jiang, Yi Tang, John Houston, Kevin E. McKenna, Kevin T. McVary, Sonic hedgehog Cascade is Required for Penile Postnatal Morphogenesis, Differentiation, and Adult Homeostasis, Biology of Reproduction, vol. 68, Issue 2, Feb. 1, 2003, pp. 423-438 (Year: 2003).*

(Continued)

*Primary Examiner* — Carl H Layno
*Assistant Examiner* — Anh-Khoa N Dinh
(74) *Attorney, Agent, or Firm* — TraskBritt (57) ABSTRACT

Described is a low voltage, pulsed electrical stimulation device for controlling expression of sonic hedgehog ("Shh"), a useful protein, by tissues. Also described are methods of enhancing expression of sonic hedgehog in cells, particularly a method of stimulating the expression and/or release of Shh in a cell having a gene encoding Shh, wherein the method includes applying a bioelectric signal of less than 50 Hz (e.g., 5 Hz, 10 Hz, or 20 Hz) at a pulse width duration of, e.g., 1 ms, to the cell (e.g., directly, indirectly, or wirelessly), and wherein the amount of Shh expression enhanced by this bioelectric signal is greater than that seen with a prior art bioelectric muscle stimulation or bioelectric muscle contraction alone as may be determined by, e.g., by an analysis of the upregulation of mRNA level/GAPDH fold gene expression in the cell.

16 Claims, 3 Drawing Sheets

(58) Field of Classification Search
CPC .. A61N 1/0456; A61N 1/0464; A61N 4/0468; A61N 1/046; A61N 1/205
See application file for complete search history.

(56) References Cited

U.S. PATENT DOCUMENTS

| | | | | |
|---|---|---|---|---|
| 2012/0310140 | A1* | 12/2012 | Kramer | A61K 9/0085 604/20 |
| 2017/0021172 | A1* | 1/2017 | Perez | A61N 1/36031 |
| 2018/0064935 | A1 | 3/2018 | Leonhardt et al. | |

OTHER PUBLICATIONS

Choe et al. "Peptide amphiphile nanofiber hydrogel delivery of Sonic hedgehog protein to the cavernous nerve to promote regeneration and prevent erectile dysfunction" Nanomedicine, Jan. 2017; 13(1): 95-101.

Dobbs et al. "Sonic hedgehog regulation of cavernous nerve regeneration and neurite formation in aged pelvic plexus" Exp Neurol. Feb. 2019; 312: 10-19.

Northwestern University "Sonic Hedgehog' Helps Regenerate CriticalNerve That Runs Along Prostate, Could HealErectile Dysfunction After Surgery" Article (Jun. 2010), Medical News Today (5 pages).

Park et al. "Sonic hedgehog intradermal gene therapy using a biodegradable poly(β-amino esters) nanoparticle to enhance wound healing" Biomaterials, vol. 33, Issue 35, Dec. 2012, pp. 9148-9156.

Paul "Protein Could Heal Erectile Dysfunction After Surgery" Article, Northwestern University News (Jun. 2010) 2 pages.

Abe et al., "Roles of the Hedgehog Signaling Pathway in Epidermal and Hair Follicle Development, Homeostasis, and Cancer" J. Dev. Biol., vol. 5, No. 4, (2017), 1-19.

Bond et al., "Sonic Hedgehog Regulates Brain-Derived Neurotrophic Factor in Normal and Regenerating Cavernous Nerves", J. Sex. Med., vol. 10, No. 3, (2013), pp. 730-737.

Chechneva et al., "Empowering Sonic Hedgehog to Rescue Brain Cells After Ischemic Stroke" Neural Regen Res., vol. 10, No. 3, (2015), pp. 360-362.

Chen et al., "Administration of Sonic Hedgehog Protein Induces Angiogenesis and has Therapeutic Effects After Stroke in Rats" Neuroscience, vol. 352, (2017), pp. 285-295.

Chen et al., "Emerging Roles of Sonic Hedgehog in Adult Neurological Diseases: Neurogenesis and Beyond", Int. J. Mol Sci., vol. 19, No. 8, (2018), 2423.

Choe et al., "Sonic Hedgehog Delivery From Self-Assembled Nanofiber Hydrogels Reduces the Fibrotic Response in Models of Erectile Dysfunction", Acta. Biomaterialia., vol. 32, (2016), pp. 89-99.

Columbia, "Implant Procedure Concepts—Pacemaker, ICD and CRT Overview," (available at columbia.edu/itc/hs/medical/hickey/docs/Pacemaker,%20ICD%20and%20CRT%20Overview%20022007.pdf).

Dassule et al., "Sonic Hedgehog Regulates Growth and Morphogenesis of the Tooth" Development, vol. 127, (2000), pp. 4775-4785.

Dobbs et al., "019 Sonic Hedgehog Promotes Cavernous Nerve Regeneration by Inducing Cavernous Nerve Sprouting and Sprouting Potential is Reduced with Age," J. Sex. Med., vol. 15, Issue 2, (2018) p. S10.

Dunaeva et al. "Hh Signaling in Regeneration of the Ischemic Heart" Cell. Mol. Life Sci., vol. 74, No. 19, (2017), pp. 3481-3490.

Fendrich et al., "Hedgehog Signaling is Required for Effective Regeneration of Exocrine Pancreas", Gastroenterology., vol. 135, No. 2, (2008), pp. 621-631.

Finco et al., "Sonic Hedgehog and WNT Signaling Promote Adrenal Gland Regeneration in Male Mice" Endocrinology, vol. 159, Issue 2, (2018), pp. 579-596.

Giarretta et al., "The Hedgehog Signaling Pathway in the Ischemic Heart, Brain, and Skeletal Muscle", Preprints, (2018), 2018080027, (doi: 10.20944/preprints201808.0027.v1).

Han et al., "Multivalent Conjugates of Sonic Hedgehog Accelerate Diabetic Wound Healing", Tissue Eng. Part A, vol. 21, No. 17-18, (2015), pp. 2366-2378.

Hopkins Medicine, "Overview of Pacemakers and Implantable Cardioverter Defibrillators(ICDs)."

Huang et al., "Overexpressing Sonic Hedgehog Peptide Restores Periosteal Bone Formation in a Murine Bone Allograft Transplantation Model" Mol. Ther., vol. 22, No. 2, (2014), pp. 430-439.

Kawagishi et al., "Sonic Hedgehog Signaling Regulates the Mammalian Cardiac Regenerative Response", J. Mol. Cell. Cardiol., vol. 123, (2018), pp. 180-184.

Lavars, "Scientists Fire up Sonic Hedgehog Gene to Spawn New Hair Regrowth Possibilities", New Atlas, (2018).

Levin et al. "Endogenous Bioelectric Signaling Networks: Exploiting Voltage Gradients for Control of Growth and Form" Annual Review of Biomedical Engineering, vol. 19, No. 1, (2017), pp. 353-387.

Li et al., "Sonic Hedgehog Signaling Induces Vascular Smooth Muscle Cell Proliferation via Induction of the G1 Cyclin-Retinoblastoma Axis" Arteriosclerosis, Thrombosis, and Vascular Biology, vol. 30, No. 9, (2010), pp. 1787-1794.

Lim et al. "Hedgehog stimulates hair follicle neogenesis by creating inductive dermis during murine skin wound healing" Nature Communications vol. 9, Article No. 4903 (2018).

Luo et al., "Sonic Hedgehog Improves Delayed Wound Healing via Enhancing Cutaneous Nitric Oxide Function in Diabetes" Am. J. Physiol. Endocrinol. Metab., vol. 297, No. 2, (2009), pp. E525-E531.

Ma et al. "Downregulation of Wnt signaling by sonic hedgehog activation promotes repopulation of human tumor cell lines", Disease Models & Mechanisms, vol. 8, (2015), pp. 385-391.

Matsumoto et al., "Expression and Role of Sonic Hedgehog in the Process of Fracture Healing with Aging", In Vivo, vol. 30, No. 2, (2016), pp. 99-105.

Nakatomi et al., "Sonic Hedgehog Signaling is Important in Tooth Root Development", J. Dent. Res., vol. 85, No. 5, (2006), pp. 427-431.

Newman, "Could Sonic Hedgehog be the Answer to Hair Loss?" Medical News Today, (2018).

Ochoa et al., "Hedgehog Signaling is Critical for Normal Liver Regeneration After Partial Hepatectomy in Mice," Hepatology, vol. 51, No. 5, (2010), pp. 1712-1723.

Podlasek et al., "Sonic Hedgehog, The Penis and Erectile Dysfunction: A Review of Sonic Hedgehog Signaling in the Penis" Curr. Pharm. Des, vol. 11, No. 31, (2005), pp. 4011-4027.

Prochazka et al., "Cocktail of Factors from Fat-derived Stem Cells Shows Promise for Critical Limb Ischemia," (Jan. 21, 2016), (available at http://www.sciencenewsline.com/news/2016012204520017.html).

Reacher "How Hedgehogs Can Help Men with ED" https://prostate.net/hedgehogs-help-with-ed/ (Feb. 21, 2019 by red64).

Salcedo et al., "Low Current Electrical Stimulation Upregulates Cytokine Expression in the Anal Sphincter," Int. J. Colorectal Dis., vol. 27, No. 2, (2012), pp. 221-225.

Song "Enhanced Bone Regeneration With Sequential Delivery of Basic Fibroblast Growth Factor and Sonic Hedgehog" Injury, vol. 42, No. 8, (2011), pp. 796-802.

Spence et al., "The Hedgehog Pathway is a Modulator of Retina Regeneration" Development, vol. 131, No. 18, (2004), pp. 4607-4621.

Sriperumbudur et al., "Hedgehog: the Key to Maintaining Adult Lung Repair and Regeneration", J. Cell. Commun. Signal, vol. 11, No. 1, (2017), pp. 95-96.

St-Jacques et al., "Sonic Hedgehog Signaling is Essential for Hair Development" Curr. Biol., vol. 8, No. 19, (1998), pp. 1058-1068.

Stenkamp et al., "Optimizing Retinal Regeneration: A Role for Sonic Hedgehog", Investigative Ophthalmology & Visual Science, vol. 51, No. 13, (2010), 4309.

(56) References Cited

OTHER PUBLICATIONS

Straface et al., "Sonic Hedgehog Regulates Angiogenesis and Myogenesis During Post-Natal Skeletal Muscle Regeneration" J. Cell. Mol. Med., vol. 13, No. 8b, (2009) pp. 2424-2435.
Su et al. "High Frequency Stimulation Induces Sonic Hedgehog Release from Hippocampal Neurons." Sci. Rep., vol. 7, (2017), 43865.
Suh et al., "Sonic Hedgehog Increases the Skin Wound-Healing Ability of Mouse Embryonic Stem Cells Through the MicroRNA 200 Family" Br. J. Pharmacol., vol. 172, No. 3, (2015), pp. 815-828.
Tae, "Researchers Discover New Skin Regeneration Mechanism", Yale News (2018).
Ueda, "Bone Regeneration Using Osteogenic Stem Cell and Sonic Hedgehog Gene", J-Stage, vol. 23, Issue 5, (2003), pp. 262-268.
University of Pennsylvania School of Medicine "Pinpointing gene that regulates repair, regeneration in adult lungs New role for hedgehog gene offers better understanding of lung disease" ScienceDaily, (2015).
Wang et al. "Sonic Hedgehog Accelerates Wound Healing Via Enhancing Cutaneous Nitric Oxide Function in Diabetes" Advances in Wound Care, vol. 2, (2011).
Wang et al., "Epicardial Regeneration is Guided by Cardiac Outflow Tract and Hedgehog Signalling" Nature, vol. 522, No. 7555, (2015).
Wu et al. "Neuroprotective Effect of Upregulated Sonic Hedgehog in Retinal Ganglion Cells Following Chronic Ocular Hypertension" IOVS, vol. 51, Issue 6, (2010).
Angeloni et al. "Regeneration of the cavernous nerve by sonic hedgehog using aligned peptide amphiphile nanofibers." Biomaterials. 2011; 32:1091-1101.
Bond et al. "Peptide amphiphile nanofiber delivery of sonic hedgehog protein to reduce smooth muscle apoptosis in the penis after cavernous nerve resection " J Sex Med. 2011; 8:78-89.
Choe et al. "Optimization of Sonic Hedgehog Delivery to the Penis from Self-Assembling Nanofiber Hydrogels to Preserve Penile Morphology after Cavernous Nerve Injury." Author Manuscript, Nanomedicine, (Aug. 2019) 20:102033.
Davis et al. "Development of a novel topical formulation of glyceryl trinitrate for the treatment of erectile dysfunction." Int J Impot Res 32, 569-577 (Dec. 2020).
Ding et al. "Dopamine Burden Induced the Inactivation of Sonic Hedgehog Signaling to Cognitive Decline in Minimal Hepatic Encephalopathy." Aging and disease vol. 8,4 442-457. Jul. 21, 2017, doi:10.14336/AD.2016.1123.
Dobbs et al. "Peptide amphiphile delivery of sonic hedgehog protein promotes neurite formation in penile projecting neurons." Nanomedicine. Oct. 2018; 14(7):2087-2094.
Fu et al. "Sonic hedgehog regulates the proliferation, differentiation, and migration of enteric neural crest cells in gut" J Cell Biol (2004) 166 (5): 673-684.

Heo et al. "Effect of Antioxidant Flavanone, Naringenin, from Citrus junos on Neuroprotection" J. Agric. Food Chem. 52, 6, 1520-1525 (2004); doi.org/10.1021/jf035079g.
Hu et al. "A systematic summary of survival and death signalling during the life of hair follicle stem cells." Stem Cell Res Ther. Aug. 11, 2021; 12(1):453.
Jeong et al. "Naringin Attenuates Autophagic Stress and Neuroinflammation in Kainic Acid-Treated Hippocampus In Vivo." EBioMedicine vol. 1, Issue 1, pp. 80-89 (Nov. 2014); doi.org/10.1016/j.ebiom.2014.11.001.
Kondo et al. "Mild Electrical Stimulation with Heat Shock Reduces Visceral Adiposity and Improves Metabolic Abnormalities in Subjects with Metabolic Syndrome or Type 2 Diabetes: Randomized Crossover Trials." Evidence-Based Complementary and Alternative Medicine vol. 2015, Article ID 354326; doi.org/10.1155/2015/354326.
Ma et al. "Sonic hedgehog signaling pathway and erectile dysfunction: Advances in studies" Zhonghua Nan Ke Xue. Sep. 2019;25(9):833-837. Chinese. PMID: 32233212 (Abstract Only).
Malave et al. "Dopaminergic co-transmission with sonic hedgehog inhibits abnormal involuntary movements in models of Parkinson's disease and L-Dopa induced dyskinesia." Commun Biol 4, 1071 (Aug. 2021).
Marrachelli et al. "Sonic hedgehog carried by microparticles corrects angiotensin II-induced hypertension and endothelial dysfunction in mice." PLoS One. Aug. 16, 2013;8(8):e72861.
Martin et al. "Peptide amphiphile nanofiber hydrogel delivery of Sonic hedgehog protein to the penis and cavernous nerve suppresses intrinsic and extrinsic apoptotic signaling mechanisms, which are an underlying cause of erectile dysfunction." Nanomedicine. (Oct. 2021) vol. 37, Article 102444.
Podlasek "Sonic hedgehog, apoptosis, and the penis." J Sex Med; vol. 6, Suppl 3, pp. 334-339 (Mar. 2009).
Scholefield et al. "A dose finding study with 0.1%, 0.2%, and 0.4% glyceryl trinitrate ointment in patients with chronic anal fissures." Gut vol. 52, (Feb. 2003): 264-269.
Yamada et al. "The Sonic Hedgehog signaling pathway regulates inferior alveolar nerve regeneration" Neuroscience Letters vol. 671, (Apr. 3, 2018), pp. 114-119.
Yu. et al. "Hair growth-promoting effect of recombinant human sonic hedgehog proteins." Biomed Dermatol 3, 7 (Dec. 2019).
Zhang et al. "Role of VIP and Sonic Hedgehog Signaling Pathways in Mediating Epithelial Wound Healing, Sensory Nerve Regeneration, and Their Defects in Diabetic Corneas" Diabetes (Jul. 2020) 69(7): 1549-1561.
Zhou et al. "Sonic hedgehog signaling in kidney fibrosis: a master communicator." Science China. Life sciences vol. 59, 9 (Sep. 2016): 920-929.

* cited by examiner

BIOELECTRIC STIMULATION FOR SONIC HEDGEHOG EXPRESSION

CROSS-REFERENCE TO RELATED APPLICATIONS

This application claims the benefit under 35 U.S.C. §119 (e) of U.S. Provisional Patent Application Ser. No. 62/834,309, filed Apr. 15, 2019, and U.S. Provisional Patent Application Ser. No. 62/988,345, filed Mar. 11, 2020, the disclosures of each of which are incorporated herein in their entirety by this reference.

The application relates generally to the field of medical devices and associated methods of treatment, and more specifically to methods of treatment involving the precise bioelectrical stimulation of a subject's tissue, optionally augmented with the administration of a composition comprising, among other things, stem cells and nutrients, useful to increase the expression and/or release of sonic hedgehog to stimulate and treat the subject, the subject's tissue(s), the subject's organ(s), and/or the subject's cells. More specifically, the application relates to a device, programmed bioelectric signaling sequences, and associated methods for the controlled expression of secreted Sonic hedgehog ("Shh"), a known powerful anti-aging and regeneration promoting protein, via precise bioelectrical signaling sequences.

BACKGROUND

Sonic hedgehog (Shh), a member of the hedgehog (Hh) family, was originally recognized as a morphogen possessing critical characters for organ development during embryogenesis. Shh has also emerged as an important modulator in adult tissues through different mechanisms such as anti-oxidation, anti-inflammation, and autophagy.

BRIEF SUMMARY

Described herein is a bioelectric stimulator particularly configured to modulate (e.g., upregulate and/or downregulate) expression and/or release of Sonic hedgehog in cellular tissue.

Also described is a method for treating or regenerating a tissue in a subject (e.g., in an animal, mammal or human), the tissue selected from the group consisting of muscle, heart, eye, liver, dental tissue and teeth, bone, adrenal gland, pancreas, brain, skin, and lung, the method comprising: applying a bioelectric signal to the tissue, which the bioelectric signal regulates (e.g., upregulates or downregulates) the expression and/or release of secreted Sonic hedgehog.

One such precise bioelectric signal to upregulate Shh is a biphasic pulse at from 50 Hz to 100 Hz at from 100 µA to 500 µA.

Another precise bioelectric signal to upregulate Shh has a frequency/pulse width duration of 5 Hz/1 ms (100 mV, biphasic, 5 Hz, 1 ms, voltage-driven system).

Another precise bioelectric signal to upregulate Shh has a frequency / pulse width duration of 10 Hz/1 ms (100 mV, biphasic, 1 ms, voltage-driven system).

Another precise bioelectric signal to upregulate Shh has a frequency/pulse width duration of 20 Hz/1 ms (100 mV, biphasic, 1 ms, voltage-driven system).

Another precise bioelectric signal to upregulate Shh has a frequency/pulse width duration of 50 Hz/1 ms (100 mV, biphasic, 1 ms, voltage-driven system).

Another precise bioelectric signal to upregulate Shh has a frequency/pulse width duration of 100 Hz/1 ms (100 mV, biphasic, 1 ms, voltage-driven system).

Further described is a method for treating a subject (e.g., in an animal, mammal or human), wherein the subject is in need of wound healing, hair regrowth and regeneration, and/or treatment of erectile dysfunction, the method comprising: applying a bioelectric signal to the subject, which signal regulates (e.g., upregulates or downregulates) the expression wherein the bioelectric signal secreted Sonic hedgehog.

One such precise bioelectric signal to upregulate Shh is a biphasic pulse at from 50 Hz to 100 Hz at from 100 µA to 500 µA. Another precise bioelectric signal to upregulate Shh has a frequency/pulse width duration of 5 Hz/1 ms (100 mV, biphasic, 1 ms, voltage-driven system). Another precise bioelectric signal to upregulate Shh has a frequency/pulse width duration of 10 Hz/1 ms (100 mV, biphasic, 1 ms, voltage-driven system). Another precise bioelectric signal to upregulate Shh has a frequency/pulse width duration of 20 Hz/1 ms (100 mV, biphasic, 1 ms, voltage-driven system). Another precise bioelectric signal to upregulate Shh has a frequency/pulse width duration of 50 Hz/1 ms (100 mV, biphasic, 1 ms, voltage-driven system). Another precise bioelectric signal to upregulate Shh has a frequency/pulse width duration of 100 Hz/1 ms (100 mV, biphasic, 1 ms, voltage-driven system).

In certain embodiments, the bioelectric stimulator is further configured to activate expression and/or release of another protein, such as stromal cell-derived factor 1 ("SDF-1"), insulin-like growth factor 1 ("IGF-1"), platelet-derived growth factor ("PDGF"), follistatin, tropoelastin, and any combination thereof.

Also described is a bioelectric stimulator including: a power source (e.g., battery, capacitor, AC, or other suitable source of electricity), and means for delivering an electrical signal to a subject's tissue (e.g., via electrode(s) or wirelessly). The bioelectric stimulator utilizes the electrical signal to precisely control Shh expression in the tissue on demand.

In certain cases, the bioelectric stimulator is programmed to produce a bioelectric signal that stimulates target tissue to express and/or release Sonic hedgehog polypeptide by the target tissue by utilizing a biphasic pulse at from 50 Hz to 100 Hz at from 100 µA to 500 µA for a period of time of from about 15 minutes to about an hour of stimulation. In certain embodiments, stimulation times of thirty (30) minutes work well, especially with up regulation. For typical treatments, this may be applied to the subject's tissue and repeated daily, or 1, 2, 3, 4, 5, 6, 7, or more times a week.

The amount of Sonic hedgehog expression enhanced by the herein described system is greater than with that seen with prior art bioelectric muscle stimulation or from muscle contraction alone.

In certain embodiments, described is a method of stimulating the expression and/or release of Shh in a cell having a gene encoding Shh, wherein the method includes applying a bioelectric signal of less than 50 Hz (e.g., 5 Hz, 10 Hz, 20 Hz, or 40 Hz) at a pulse width duration of, e.g., 1 ms, to the cell (e.g., directly or wirelessly), and wherein the amount of Shh expression enhanced by this bioelectric signal is greater than that seen with a prior art bioelectric muscle stimulation or bioelectric muscle contraction alone (e.g., "ESTIM") as may be determined by, e.g., by an analysis of the upregulation of mRNA level/GAPDH fold gene expression in the cell.

In certain cases, a method of using the bioelectric stimulator to stimulate tissue of a subject includes connecting (directly or wirelessly) the bioelectric stimulator to the target tissue or cells of the subject. The target tissue may be selected from, e.g., the group consisting of muscle, heart, eye, liver, pancreas, brain, skin, and lung.

In certain cases, the subject is interested in body building.

In certain cases, the subject has been diagnosed as is in need of wound healing, hair regeneration, and/or treatment of erectile dysfunction.

A preferred system includes: a bioelectric stimulator that controls/stimulates the release/production of Sonic hedgehog by a target cell or tissue. The stimulator may be associated with (e.g., connected to) the organ or tissue to be treated with a pacing infusion lead (available from Nanoscribe of Eggenstein-Leopoldshafen, Germany) or wirelessly. In certain cases, the interface with the subject's tissue may be by a conductive soft wrap.

The stimulator can be designed to externally deliver all regeneration promoting signals wirelessly to the subject's organ(s), tissue(s), and/or cells. In certain embodiments, a micro infusion pump may be included in the system to deliver other supportive substances (such as stem cells) in greater volume more quickly.

While not intending to be bound by theory, the described system utilizes precise bioelectric signaling sequences that appear to communicate with the cells, cell membranes, and DNA of the subject to cause the cells to produce high volumes of the Sonic hedgehog protein. Potential indications include muscle regeneration and treatment, heart treatment and regeneration, eye treatment and regeneration, liver treatment and regeneration, pancreas treatment and regeneration, brain (and other nervous tissue) protection, treatment, and regeneration, wound healing, hair regeneration, skin treatment and regeneration, lung treatment and regeneration, and treatment of erectile dysfunction. A goal is to use the described technology to help patients keep their own organs, regenerated back to full health, instead of getting artificial, different species, or donor transplant implants

DETAILED DESCRIPTION

In certain embodiments, described is a bandage wrap that is applied to the affected region. A micro-stimulator may be located conveniently in the bandage wrap and is utilized to distribute specific bioelectric signals to the affected tissue and nerves that regulate various protein expressions for stem cell homing, stem cell proliferation, stem cell differentiation, blood vessel formation, blood circulation improvement, muscle function repair, and DNA repair.

Figure 1:
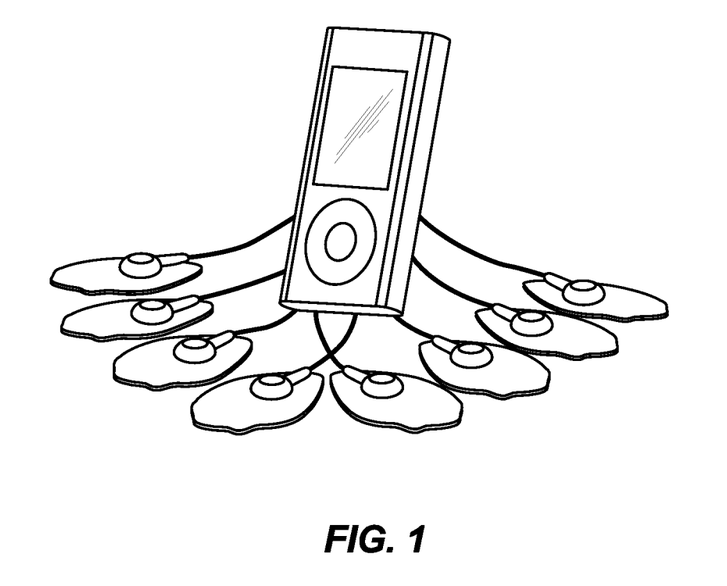
FIG. 1 depicts a programmed bioelectric stimulator for delivery to a subject connected to multiple soft conductive electrode pads.
Figure 2:
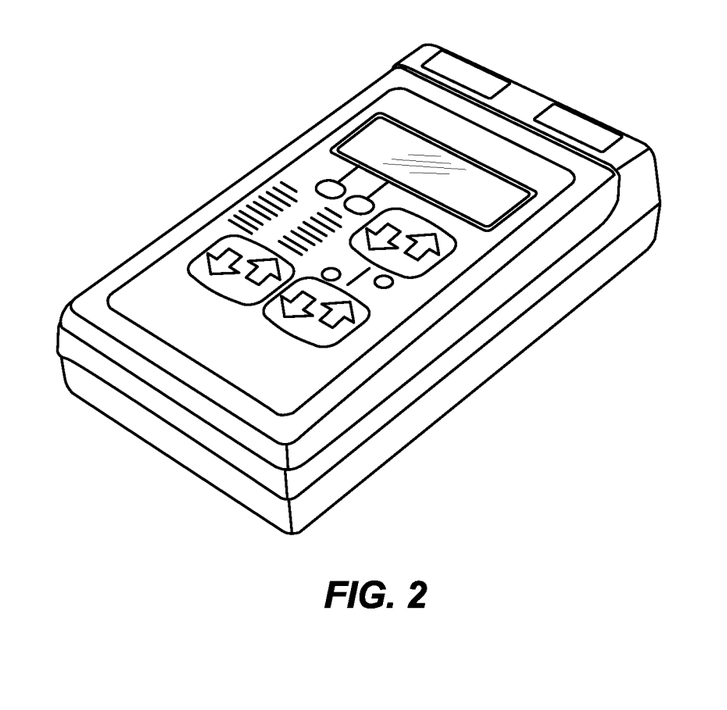
FIG. 2 depicts a programmed bioelectric stimulator as described herein.
Figure 3:
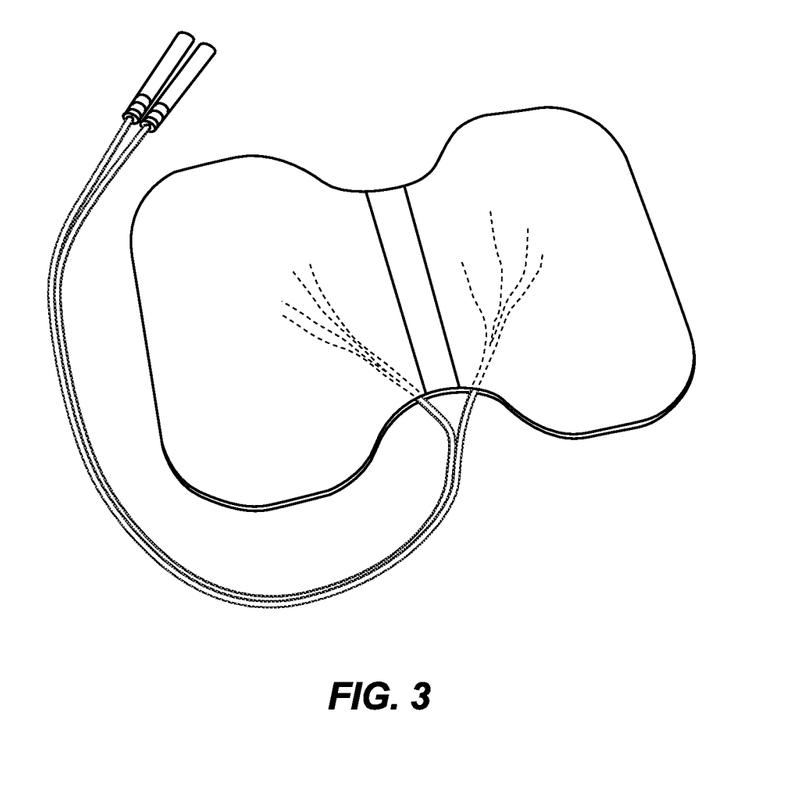
FIG. 3 depicts a conductive soft wrap for use with the system.
Figure 4:
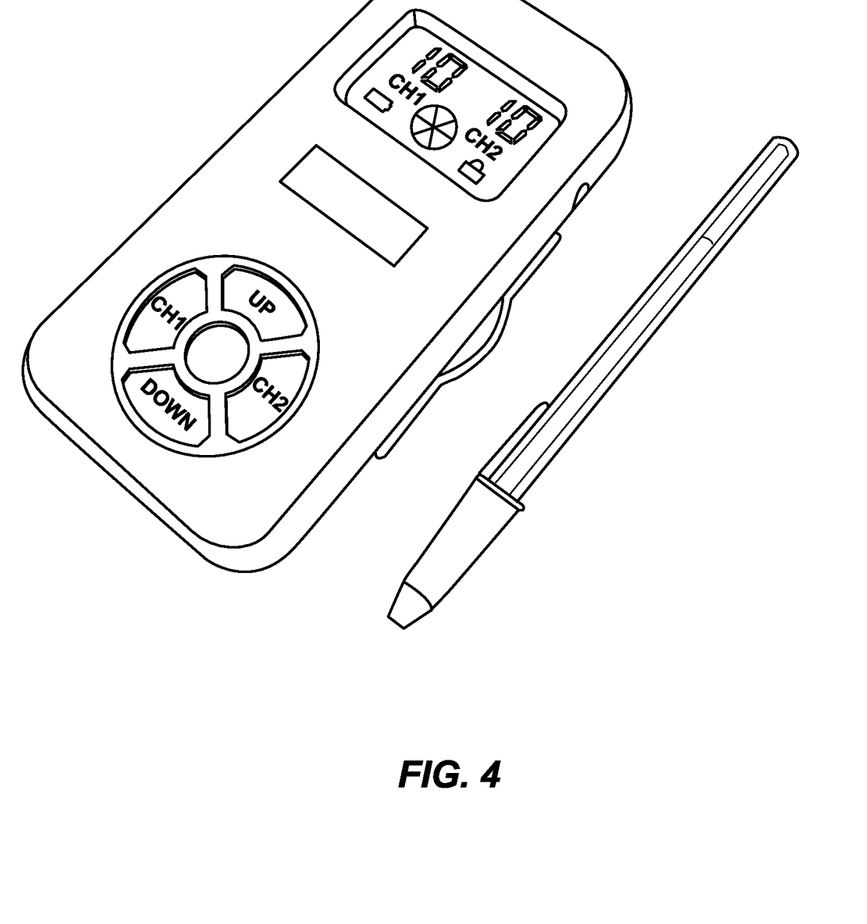
FIG. 4 depicts a programmed bioelectric stimulator depicted alongside a pen.

Referring now to FIG. 1, depicted is a stimulator for use in treating a human. The depicted device is about the size of a pen (FIG. 4) and is programmable.

Preferably, the system utilizes a bioelectric stimulator programmed to control expression and/or release of secrete Sonic hedgehog. As described in Su, Y. et al. High frequency stimulation induces sonic hedgehog release from hippocampal neurons. Sci. Rep. 7, 43865; doi: 10.1038/srep43865 (2017), the contents of which are incorporated herein by this reference, high, but not low, frequency stimulation induces Shh release from neurons, but not from astrocytes.

A bench top stimulator (e.g., a Mettler Model 240 Stimulator from Mettler Electronics of Anaheim, Calif., US) may be pre-programmed with the bioelectric signaling sequence(s) for controlling the expression and/or release of Shh.

In some embodiments (e.g., for the regulation of the production of new neurons or new bone growth), the bioelectric signaling can further be used to modulate (e.g., upregulate) by the subject's cells the production of other molecules in addition to Shh and/or the recruitment of stem cells. See, e.g., US 20180064935 A1 to Leonhardt et al. (Mar. 8, 2018), the contents of which are incorporated herein by this reference.

For treating and/or regenerating heart utilizing Shh, see, e.g., Kawagishi et al., "Sonic hedgehog signaling regulates the mammalian cardiac regenerative response", *J Mol Cell Cardiol.* 2018 Oct; 123:180-184, doi: 10.1016/j.yjmcc.2018.09.005. Epub 2018 Sep 17, Levin et al. "Endogenous Bioelectric Signaling Networks: Exploiting Voltage Gradients for Control of Growth and Form" *Annual Review of Biomedical Engineering* 19(1):353-387, June 2017, Wang et al. "Epicardial regeneration is guided by cardiac outflow tract and Hedgehog signalling" *Nature* 522 (7555), May 2015, and Dunaeva et al. "Hh signaling in regeneration of the ischemic heart" *Cell Mol Life Sci.* 2017; 74(19): 3481-3490, the contents of each of which are incorporated herein by this reference.

For treating and/or regenerating liver utilizing Shh, see, e.g., Ochoa et al., "Hedgehog signaling is critical for normal liver regeneration after partial hepatectomy in mice", *Hepatology.* 2010 May; 51(5): 1712-1723. doi: 10.1002/hep.23525, the contents of which are incorporated herein by this reference.

For treating and/or regenerating pancreas utilizing Shh, see, e.g., Fendrich et al., "Hedgehog Signaling Is Required for Effective Regeneration of Exocrine Pancreas", Gastroenterology. 2008 Aug; 135(2): 621-631 and Frendrich et al. "Hedgehog Signaling Is Required for Effective Regeneration of Exocrine Pancreas" Gastroenterology 135(2):621-31 May 2008, the contents of each of which are incorporated herein by this reference.

For protecting, treating, and regenerating the brain, neurons and nervous tissue utilizing Shh (including recovery from stroke), see, e.g., Shang-Der Chen et al., "Emerging Roles of Sonic Hedgehog in Adult Neurological Diseases: Neurogenesis and Beyond", *Int J Mol Sci.* 2018 Aug; 19(8): 2423, Chechneva et al "Empowering sonic hedgehog to rescue brain cells after ischemic stroke" *Neural Regen Res.* 2015 Mar; 10(3): 360-362, doi: 10.4103/1673-5374.153677, Wu et al. "Neuroprotective Effect of Upregulated Sonic Hedgehog in Retinal Ganglion Cells Following Chronic Ocular Hypertension" *IOVS* June 2010 Volume 51, Issue 6, and Chen et al. "Administration of sonic hedgehog protein induces angiogenesis and has therapeutic effects after stroke in rats" *Neuroscience.* 2017 Jun 3; 352:285-295, doi: 10.1016/j.neuroscience.2017.03.054. Epub 2017 Apr 5, the contents of each of which are incorporated herein by this reference. A preferred cell for treating and regenerating the brain is the neuron. See, also, Giarretta, I.; Gaetani, E.; Tondi, P.; Asahara, T.; Pola, R. The Hedgehog Signaling Pathway in the Ischemic Heart, Brain, and Skeletal Muscle. *Preprints* 2018, 2018080027 (doi: 10.20944/ preprints201808.0027.v1), the contents of which are incorporated herein by this reference.

For treating and/or regenerating eye utilizing Shh, see, e.g., the herein incorporated Wu et al. (2010), Stenkamp et al., "Optimizing Retinal Regeneration: A Role for Sonic Hedgehog", *Investigative Ophthalmology & Visual Science* April 2010, Vol. 51(13), 4309 and Spence et al. "The hedgehog pathway is a modulator of retina regeneration" *Development*, 2004 Sep; 131(18):4607-21, the contents of each of which are incorporated herein by this reference.

For treating and/or regenerating teeth and tooth roots utilizing Shh, see, e.g., Dassule et al. "Sonic hedgehog regulates growth and morphogenesis of the tooth" *Development*, 2000 127: 4775-4785 and Nakamoti et al. "Sonic hedgehog signaling is important in tooth root development", *J Dent Res.* 2006 May; 85(5):427-31, the contents of each of which are incorporated herein by this reference.

For treating and/or regenerating bone utilizing Shh, see, e.g., Huang et al., "Overexpressing sonic hedgehog peptide restores periosteal bone formation in a murine bone allograft transplantation model" *Mol Ther.* 2014 Feb; 22(2):430-439. doi: 10.1038/mt.2013.222. Epub 2013 Oct 3, K. Song "Enhanced bone regeneration with sequential delivery of basic fibroblast growth factor and sonic hedgehog" *Injury* 2011 Aug; 42(8):796-802. doi: 10.1016/j. injury.2011.02.003. Epub (2011 Mar 1), M. Ueda, "Bone regeneration using osteogenic stem cell and sonic hedgehog gene", *J-Stage* 2003 Volume 23 Issue 5 Pages 262-268, and Matsumoto et al. "Expression and Role of Sonic Hedgehog in the Process of Fracture Healing with Aging", *In Vivo* March-April 2016, 30(2): 99-105, the contents of each of which are incorporated herein by this reference.

For wound healing utilizing Shh, see, e.g., the previously incorporated Chen et al. (2017), Han et al., "Multivalent Conjugates of Sonic Hedgehog Accelerate Diabetic Wound Healing", *Tissue Eng Part A.* 2015 Sep; 21(17-18): 2366-78, doi: 10.1089/ten.TEA.2014.0281, Luo et al. "Sonic hedgehog improves delayed wound healing via enhancing cutaneous nitric oxide function in diabetes" *Am J Physiol Endocrinol Metab.* 2009 Aug; 297(2): E525-E531, and Wang et al. "Sonic Hedgehog Accelerates Wound Healing Via Enhancing Cutaneous Nitric Oxide Function in Diabetes" *Advances in Wound Care: Volume* 2, (May 9, 2011), the contents of each of which are incorporated herein by this reference.

For hair regeneration utilizing Shh, see, e.g., N. Lavars, "Scientists fire up sonic hedgehog gene to spawn new hair regrowth possibilities", *New Atlas* (Nov. 28, 2018), Lim et al. "Hedgehog stimulates hair follicle neogenesis by creating inductive dermis during murine skin wound healing" *Nature Communications* Vol. 9, Article number: 4903 (2018), T. Newman "Could sonic hedgehog be the answer to hair loss?" *Medical News Today* (Dec. 1, 2018), St-Jacques et al. "Sonic hedgehog signaling is essential for hair development" *Curr Biol.* 1998 Sep 24; 8(19): 1058-68, Abe et al. "Roles of the Hedgehog Signaling Pathway in Epidermal and Hair Follicle Development, Homeostasis, and Cancer" *J Dev Biol.* 2017 Dec; 5(4): 12., the contents of each of which are incorporated herein by this reference. A preferred treatment tissue for regenerating hair is the follicle.

For treating and/or regenerating skin utilizing Shh, see, e.g., the previously incorporated Abe et al. (2017), Suh et al. "Sonic hedgehog increases the skin wound-healing ability of mouse embryonic stem cells through the microRNA 200 family" *Br J Pharmacol.* 2015 Feb; 172(3): 815-828, and J. Tae, "Researchers discover new skin regeneration mechanism", *Yale News* Dec. 4, 2018, the contents of which are incorporated herein by this reference.

For treating erectile dysfunction utilizing Shh, see, e.g., Choe et al., "Sonic hedgehog delivery from self-assembled nanofiber hydrogels reduces the fibrotic response in models of erectile dysfunction", *Acta Biomaterialia* Volume 32, 1 March 2016, pp. 89-99, Bond et al. "Sonic Hedgehog Regulates Brain-Derived Neurotrophic Factor in Normal and Regenerating Cavernous Nerves". *J Sex Med* 2013; 10(3):730-737; Podlasek et al. "Sonic hedgehog, the penis and erectile dysfunction: a review of sonic hedgehog signaling in the penis" *Curr Pharm Des.* 2005; 11(31):4011-27; and Dobbs et al. "019 Sonic Hedgehog Promotes Cavernous Nerve Regeneration by Inducing Cavernous Nerve Sprouting and Sprouting Potential is Reduced with Age" *J Sex Med* Feb. 2018Volume 15, Issue 2, Supplement 1, Page S10, the contents of each of which are incorporated herein by this reference.

For treating and/or regenerating lung utilizing Shh, see, e.g., Sriperumbudur et al., "Hedgehog: the key to maintaining adult lung repair and regeneration", *J Cell Commun Signal*, 2017 Mar; 11(1): 95-96, published online 2016 Dec 12. doi: 10.1007/s12079-016-0365-3 and University of Pennsylvania School of Medicine "Pinpointing gene that regulates repair, regeneration in adult lungs: New role for hedgehog gene offers better understanding of lung disease" *ScienceDaily*, 5 October 2015, the contents of each of which are incorporated herein by this reference.

For treating and/or regenerating muscle utilizing Shh, see, e.g., Straface et al., "Sonic hedgehog regulates angiogenesis and myogenesis during post-natal skeletal muscle regeneration" *J Cell Mol Med.* 2009 Aug; 13(8b): 2424-2435, the contents of which are incorporated herein by this reference.

For treating and/or regenerating vascular smooth muscle cells utilizing Shh, see, e.g., Li et al., "Sonic Hedgehog Signaling Induces Vascular Smooth Muscle Cell Proliferation via Induction of the G1 Cyclin-Retinoblastoma Axis" *Arteriosclerosis, Thrombosis, and Vascular Biology* 2010; 30(9):1787-1794 (Sep. 2010), the contents of which are incorporated herein by this reference.

For treating and/or regenerating the adrenal gland utilizing Shh, see, e.g., Finco et al., "Sonic Hedgehog and WNT Signaling Promote Adrenal Gland Regeneration in Male Mice" *Endocrinology*, Vol. 159, Issue 2, Feb. 2018, pp 579-596, the contents of which are incorporated herein by this reference.

In certain embodiments, e.g., in the treatment of a subject suffering from cancer, down regulation of the expression and/or release of Sonic hedgehog may be of benefit. See, e.g., Ma et al. "Downregulation of Wnt signaling by sonic hedgehog activation promotes repopulation of human tumor cell lines", Disease Models & Mechanisms 2015 8: 385-391; doi: 10.1242/dmm.018887, the contents of which are incorporated herein by this reference.

The bioelectric stimulator may also modulate the expression (e.g., upregulate expression of SDF-1, IGF-1, PDGF, follistatin, and tropoelastin).

Sonic hedgehog is as described above. Follistatin promotes muscle growth and counteracts myostatin. SDF-1 is generally for recruiting stem cells and maturing blood vessels. IGF-1 is for DNA repair. PDGF is a second stem cell homing factor and helps tissue regeneration. Any one of the protein expression signals work well on their own for organ regeneration, but they work better together. SDF-1 is a powerful regeneration protein, as is IGF-1.

Various bioelectric signals for modulating proteins are disclosed in US 20180064935 to Leonhardt et al. (Mar. 8, 2018), the contents of which are incorporated herein by this reference.

The pacing infusion lead may be constructed or purchased from the same suppliers that build standard heart pacemaker leads. Pacing infusion leads may be purchased from a variety of OEM vendors. The pacing infusion lead may, for example, be a standard one currently used in heart failure pacing studies in combination with drug delivery.

An infusion and electrode wide area patch may be constructed by cutting conduction polymer to a desired shape, and forming plastic into a flat bag with outlet ports in strategic locations.

Micro stimulators may be purchased or constructed in the same manner heart pacemakers have been made since the 1960's. When used with a micro infusion pump, such pumps can be purchased or produced similar to how they have been produced for drug, insulin, and pain medication delivery since the 1970's. The programming computer can be standard laptop computer. The programming wand customary to wireless programming wands may be used to program heart pacers.

Both wireless non-invasive and/or implantable wire lead ("electrode") based means may be used to deliver the regeneration and healing promoting bioelectric signals to target organs.

A wireless, single lumen infusion pacing lead or infusion conduction wide array patch may all be used to deliver the regeneration signals and substances to the organ of interest to be treated or they may be used in combination.

A re-charging wand for use herein is preferably similar to the pacemaker re-charging wand developed by Alfred Mann in the early 1970's for recharging externally implantable pacemakers.

Bioelectric stimulation can be done with the described microstimulator, which can have a pacing infusion lead with, e.g., a corkscrew lead placed/attached at, e.g., the center of the tissue to be stimulated and/or treated.

The microstimulator is actuated and runs through programmed signals to signal the release of, e.g., Sonic hedgehog. In such a method, the electrical signal may be measured three (3) mm deep into the tissue.

Relationship Between The Components:

The micro voltage signal generator is attached to the pacing infusion lead with, e.g., a corkscrew tip, deep vein stimulation lead (Medtronic) (e.g., for bioelectric stimulation of the brain), or conductive polymer bandage or patch to the tissue or organ to be treated. An external signal programmer may be used to program the micro voltage signal generator with the proper signals for treatment including the Sonic hedgehog producing signal. The device battery may be re-chargeable with an external battery charging wand.

The essential elements are the micro voltage signal generator and the means for delivering the signal to the target tissue.

The signal generator may be external or internal. The transmission of the signal may be wireless, via liquid and/or via wires.

The tissue contact interface may be, e.g., a patch or bandage or may be via electrodes or leads. FDA cleared gel tape electrodes (Mettler) may be used for skin delivery. Electro acupuncture needles may be used to ensure the signals positively reach target tissues under the skin.

The invention is further described by the following illustrative Examples.

EXAMPLES

Studies were performed on osteoblasts, focusing on the expression of Sonic hedgehog (SHH). The results as are follows.

SHH had a 2.19 E+05 mRNA level/Glyceraldehyde-3-phosphate dehydrogenase (GAPDH—a default reference gene in quantitative mRNA profiling) fold gene upregulation at a frequency / pulse width duration of 5 Hz/1 ms.

A Table of results on osteoblasts at different frequencies follows:

| Fold Gene Expression | |
| --- | --- |
| Sample | SHH |
| 5 Hz/1 ms | 3.17E+05 |
| 10 Hz/1 ms | 1.27E+05 |
| 20 Hz/1 ms | 1.37E+05 |
| 50 Hz/1 ms | 1.53E+05 |
| 100 Hz/1 ms | 8.47E+04 |

REFERENCES (The contents of the entirety of each of which is incorporated herein by this reference.)

Columbia, "Implant Procedure Concepts - Pacemaker, ICD and CRT Overview," columbia.edu/itc/hs/medical/hickey/docs/Pacemaker,%20ICD%20and%20CRT%20Overview%2 0022007.pdf.

Dobbs et al., "019 Sonic Hedgehog Promotes Cavernous Nerve Regeneration by Inducing Cavernous Nerve Sprouting and Sprouting Potential is Reduced with Age," *J. Sex. Med.* February 2018, Volume 15, Issue 2, Supplement 1, Page S10.

Hopkins Medicine, "Overview of Pacemakers and Implantable Cardioverter Defibrillators(ICDs)."

Ochoa et al., "Hedgehog signaling is critical for normal liver regeneration after partial hepatectomy in mice," *Hepatology.* 2010 May; 51(5): 1712-1723. doi: 10.1002/hep.23525.

Prochazka et al., "Cocktail of Factors from Fat-derived Stem Cells Shows Promise for Critical Limb Ischemia," www.sciencenewsline.com/news/2016012204520017.html (Jan. 21, 2016).

Salcedo et al., "Low current electrical stimulation upregulates cytokine expression in the anal sphincter," *Int. J. Colorectal Dis.,* 2012 Feb;27(2):221-5. doi: 10.1007/s00384-011-1324-3. Epub (Oct 2011).

Su et al. "High frequency stimulation induces sonic hedgehog release from hippocampal neurons." *Sci Rep* 7, 43865 (2017).

What is claimed is:

1. A method for upregulating expression of Sonic hedgehog polypeptide in a tissue of a subject, the tissue selected from the group consisting of muscle, heart, liver, pancreas, skin, and lung, the method comprising:
    utilizing a bioelectric stimulator to apply a bioelectric signal to the tissue that upregulates the expression of Sonic hedgehog polypeptide in the tissue,
    wherein the bioelectric signal that upregulates expression of Sonic hedgehog in the tissue comprises: a biphasic pulse with a frequency range of 50 Hz to 100 Hz at a current greater than or equal to 100 µA at the tissue.

2. A method of using a bioelectric stimulator to stimulate tissue of a subject, wherein the bioelectric stimulator is programmed to produce a bioelectric signal that upregulates expression of Sonic hedgehog in the tissue, the bioelectric signal comprising: a biphasic pulse with a frequency range of 50 Hz to 100 Hz at a current greater than or equal to 100 µA at the tissue, and wherein the subject is in need of wound healing, hair regeneration, and/or treatment of erectile dysfunction, the method comprising:

connecting the bioelectric stimulator to the target tissue of the subject, and actuating the bioelectric stimulator to produce the programmed bioelectric signal so as to upregulate expression of Sonic hedgehog in the tissue.

3. The method according to claim 2, wherein the bioelectric signal provides a current of from 100 µA to 500 µA as measured three (3) mm deep into the tissue.

4. The method according to claim 2, wherein the bioelectric signal has a frequency/pulse width duration of 50 Hz/1 ms.

5. The method according to claim 2, wherein the bioelectric signal has a frequency/pulse width duration of 100 Hz/1 ms.

6. A method of stimulating the expression of sonic hedgehog ("Shh") in a cell having a gene encoding Shh, wherein the method comprises:

applying to the cell a bioelectric signal of 5 Hz, 10 Hz, or 20 Hz at an adequate pulse width duration, wherein the amount of Shh expression enhanced by this bioelectric signal is greater than that seen with a generic bioelectric cell stimulation alone as may be determined by an analysis of the upregulation of mRNA level/GAPDH fold gene expression in the cell in each situation.

7. The method according to claim 6, wherein the bioelectric signal has a frequency/pulse width duration of 5 Hz/1 ms.

8. The method according to claim 6, wherein the bioelectric signal has a frequency/pulse width duration of 10 Hz/1 ms.

9. The method according to claim 6, wherein the bioelectric signal has a frequency/pulse width duration of 20 Hz/1 ms.

10. A bioelectric stimulator programmed to produce at least one bioelectric signal that upregulates expression of Sonic hedgehog polypeptide in a target tissue, wherein the bioelectric signal is selected from the group consisting of a biphasic pulse at a frequency of 5 Hz with a pulse width duration of 1 ms at a current greater than or equal to 100 pA when measured three (3) mm deep into the target tissue, a biphasic pulse at a frequency of 10 Hz with a pulse width duration of 1 ms at a current greater than or equal to 100 pA when measured three (3) mm deep into the target tissue, a biphasic pulse at a frequency of 20 Hz with a pulse width duration of 1 ms at a current greater than or equal to 100 pA when measured three (3) mm deep into the target tissue, and a biphasic pulse at a frequency of 40 Hz with a pulse width duration of 1 ms at a current greater than or equal to 100 pA when measured three (3) mm deep into the target tissue.

11. The bioelectric stimulator of claim 10, wherein the bioelectric signal has a frequency of 5 Hz with a pulse width duration of 1 ms.

12. The bioelectric stimulator of claim 10, wherein the bioelectric signal has a frequency of 20 Hz with a pulse width duration of 1 ms.

13. The bioelectric stimulator of claim 10, wherein the bioelectric signal has a frequency of 40 Hz with a pulse width duration of 1 ms.

14. A method of using the bioelectric stimulator of claim 10 to stimulate tissue of a subject, wherein the subject is in need of wound healing, hair regeneration, and/or treatment of erectile dysfunction, the method comprising:

connecting the bioelectric stimulator to tissue of the subject, and actuating the bioelectric stimulator to produce the programmed bioelectric signal so as to upregulate expression of Sonic hedgehog in the tissue.

15. The method according to claim 14, wherein the bioelectric signal provides a current of from 100 µA to 500 µA as measured three (3) mm deep into the tissue.

16. The method according to claim 14, wherein the bioelectric signal has a frequency/pulse width duration of 5 Hz/1 ms.

* * * * *

UNITED STATES PATENT AND TRADEMARK OFFICE
CERTIFICATE OF CORRECTION

PATENT NO. : 11,433,231 B2
APPLICATION NO. : 16/847351
DATED : September 6, 2022
INVENTOR(S) : Howard Leonhardt It is certified that error appears in the above-identified patent and that said Letters Patent is hereby corrected as shown below:

In the Claims

| | | | |
|---|---|---|---|
| Claim 10, | Column 10, | Line 5, | change "pA when" to --µA when-- |
| Claim 10, | Column 10, | Line 9, | change "100 pA" to --100 µA-- |
| Claim 10, | Column 10, | Line 13, | change "100 pA" to --100 µA-- |
| Claim 10, | Column 10, | Line 17, | change "100 pA" to --100 µA-- |

Signed and Sealed this
Eighteenth Day of April, 2023

Katherine Kelly Vidal
*Director of the United States Patent and Trademark Office*